United States Patent
De Keyzer et al.

(10) Patent No.: US 6,465,557 B1
(45) Date of Patent: Oct. 15, 2002

(54) HOT MELT PRESSURE SENSITIVE POSITIONING ADHESIVE

(75) Inventors: Noël Raymond Maurice De Keyzer, Ottignies (BE); Carolyn Ann Stoner, Houston, TX (US)

(73) Assignee: Kraton Polymers U.S. LLC, Houston, TX (US)

( * ) Notice: Subject to any disclaimer, the term of this patent is extended or adjusted under 35 U.S.C. 154(b) by 0 days.

(21) Appl. No.: 09/599,131

(22) Filed: Jun. 22, 2000

Related U.S. Application Data

(60) Provisional application No. 60/141,145, filed on Jun. 25, 1999.

(51) Int. Cl.$^7$ .......................... C08L 53/02; A61L 15/58
(52) U.S. Cl. ........................ 524/474; 524/487; 525/505
(58) Field of Search ................................. 524/474, 505, 524/487; 525/88

(56) References Cited

U.S. PATENT DOCUMENTS

| | | | |
|---|---|---|---|
| 4,136,699 A | 1/1979 | Collins et al. | 128/290 R |
| 4,526,577 A | 7/1985 | Schmidt, Jr. et al. | 604/366 |
| 4,857,594 A | 8/1989 | Lakshmanan et al. | 525/98 |
| 5,163,976 A | 11/1992 | Ravipati et al. | 51/295 |
| 5,459,193 A | 10/1995 | Anderson et al. | 524/505 |
| 5,486,387 A | 1/1996 | Mueller | 428/34.7 |
| 5,618,883 A | 4/1997 | Plamthottam et al. | 525/98 |
| 5,703,162 A | 12/1997 | Anderson | 525/89 |
| 5,741,840 A | 4/1998 | Lindquist et al. | 524/271 |
| 5,777,043 A | 7/1998 | Shafer et al. | 525/339 |

FOREIGN PATENT DOCUMENTS

| | | |
|---|---|---|
| AU | 90/631250 | 4/1991 |
| DE | 3705992 | 8/1987 |
| EP | 0428017 A2 | 10/1990 |
| EP | 0397100 | 11/1990 |
| EP | 0431391 | 6/1991 |
| EP | 0525251 A1 | 12/1991 |
| EP | 0802251 A1 | 4/1996 |
| JP | 57055980 | 4/1982 |
| JP | 61152759 | 7/1986 |
| JP | 01256583 | 10/1989 |
| JP | 03162730 | 7/1991 |
| JP | 03258844 | 11/1991 |
| JP | 05002325 | 1/1993 |
| JP | 05008954 | 2/1993 |
| JP | 06228527 | 8/1994 |
| JP | 06228529 | 8/1994 |
| JP | 08/073822 | 9/1994 |
| JP | 07304911 | 11/1995 |
| JP | 2791396 | 8/1998 |
| JP | 10298514 | 11/1998 |
| WO | WO 95/30721 | 11/1995 |

OTHER PUBLICATIONS

Cigana et al., *Macromolecules*, 30(14) pp. 4163–4169, 1997 (Abstract).

Nishikawa et al., *Polym. Prepr. (ACS, Div. Polym. Chem.)*, 37(2), pp. 702–703, 1996 (Abstract).

*Primary Examiner*—Jeffrey Mullis

(57) ABSTRACT

The present invention is a hot melt pressure sensitive positioning adhesive for use with an absorbent article. The adhesive comprises:

(a) from greater than 6 to less than 15 percent by weight of the total of (a), (b) and (c) of a hydrogenated styrene-(butadiene and/or isoprene)-styrene block copolymer having a vinyl content of greater than 50% by weight; and (b) from 50 to 80 percent by weight of the total of (a), (b) and (c) of a tackifying resin which has an aromaticity such that the MMAP cloud point is at least 45° C.; and (c) from 5 to 35 percent by weight of the total of (a), (b) and (c) of a plasticizer.

13 Claims, No Drawings

HOT MELT PRESSURE SENSITIVE POSITIONING ADHESIVE

This application claims the benefit of U.S. Provisional Application No. 60/141,145, filed Jun. 25, 1999, the entire disclosure of which is hereby incorporated by reference.

FIELD OF THE INVENTION

This invention relates to hot melt pressure sensitive positioning adhesives for use with absorbent articles which are based on hydrogenated block copolymers of styrene and butadiene or isoprene and exhibit improved viscosity and viscosity/temperature profile.

BACKGROUND OF THE INVENTION

Positioning adhesives are used on disposable articles (absorbent articles) such as sanitary napkins, incontinent pads, bed pads, feminine pads, panty shields, and diaper inserts, where an adhesive layer is used to attach the article to a woven fabric substrate such as a supporting undergarment or bed sheet. The positioning adhesive is commonly applied to a release liner and transfer coated to the garment facing surface of the disposable article. The positioning adhesive must be capable of attaching to the undergarment to hold the article in place without transferring to or otherwise being deposited on the undergarment. Furthermore, the adhesive must not discolor, damage, or disturb the fibers of the garment.

The positioning adhesive must be a pressure sensitive adhesive that has an application viscosity that permits it to readily flow onto and partially penetrate the particular surface to which it is applied. It must have good bond strength and high tack for initial placement of the article on the undergarment but also must have the ability to avoid loss of adhesion over time due to temperature conditions. Finally, these articles are sometimes used for long periods of times at body temperature and they can have the drawback that the hot melt adhesive gradually softens and penetrates into the undergarment to which the article is adhering. In this case, the adhesive force greatly increases and the cohesive force is reduced. This causes the adhesive layer to suffer cohesion breakdown when the article is removed and some adhesive remains on the undergarment. Prevention of this deposit of adhesive on the undergarment is accordingly a necessary prerequisite for a successful positionable hot melt adhesive composition.

Block copolymers of styrene and dienes such as butadiene or isoprene have been used for a number of years in positionable hot melt adhesive formulations. More recently, the material of choice for such adhesives in feminine care applications has been hydrogenated block copolymers of styrene and butadiene such as KRATON® G1650 SEBS hydrogenated styrene-butadiene-styrene) block copolymer. These SEBS block copolymers that have been used in this application (see U.S. Pat. No. 5,777,031) generally have a vinyl content of 18 to 50% by weight. KRATON G1650 has a vinyl content of about 35% by weight. Formulations based on these SEBS block copolymers have been found to have excellent adhesion to fabrics like cotton and nylon and have the advantage that they leave no residue after peeling. The application viscosity i.e. melt viscosity, of formulations using these polymers is acceptable but it would be advantageous to have a positionable adhesive formulation which has a lower melt viscosity in order to be able to lower the application temperature. This reduces the risk of degradation, char forming, and filter plugging. This also results in energy and cost savings, decreases maintenance costs, and reduces the amount of odor due to any volatiles coming from the adhesive formulation. The present invention provides such an improved positionable hot melt adhesive formulation.

SUMMARY OF THE INVENTION

The present invention is a hot melt pressure sensitive positioning adhesive for use with an absorbent article. The adhesive comprises:

(a) from greater than 6 to less than 15 percent by weight of the total of (a), (b) and (c) of a hydrogenated styrene-(butadiene and/or isoprene)-styrene block copolymer having a vinyl content of from greater than 50 to 90%, preferably 70 to 80% by weight of the total butadiene and/or isoprene block; and (b) from 50 to 80 percent by weight of the total of (a), (b) and (c) of a tackifying resin which has an aromaticity such that the MMAP is at least 45° C.; and (c) from 5 to 35 percent by weight of the total of (a), (b), and (c) of a plasticizer.

The term "vinyl content" refers to the fact that a conjugated diene may be polymerized via 1,2-addition (in the case of butadiene—it would be 3,4-addition or 1,2-addition in the case of isoprene). Although a pure "vinyl" group is formed only in the case of 1,2-addition polymerization of 1,3-butadiene, the effects of 3,4-addition polymerization of isoprene (and similar addition for other conjugated dienes) on the final properties of the block copolymer will be similar. The term "vinyl" refers to the presence of a pendant vinyl group on the polymer chain. The purpose here is to introduce chain branching and to reduce the size of the main polymer backbone (since some of the carbons in the diene are in the pendant group) which reduces the end to end length of the molecule and, in turn, its viscosity in the cement.

DETAILED DESCRIPTION OF THE INVENTION

One of the primary components of the positioning adhesive composition of the present invention is the above-described hydrogenated block copolymer which has two polystyrene endblocks and a saturated or hydrogenated polybutadiene and/or polyisoprene midblock. This hydrogenated base block copolymer provides the primary load bearing capability of the adhesive composition. It is important that the polymer be hydrogenated so that the structural integrity of the polymer is preserved even if outside forces that cause degradation are encountered. The block copolymer may be hydrogenated as generally described in the prior art, preferably so as to reduce at least 90 percent of any olefinic double bonds in the polymer chains. Suitably at least 50 percent, preferably at least 70 percent, and more preferably at least 90 percent, most preferably at least 95 percent of the original olefinic unsaturation is hydrogenated.

Polymerisation of butadiene (and/or isoprene) must produce a polymer block with a high vinyl content. This typically involves anionic polymerisation in an apolar solvent in the presence of a structure modifier, as is well known in the art. The vinyl content should be greater than 50% by weight, preferably 50–90%, more preferably 70 to 80%wt. At 50% or below, the polymer viscosity is similar to conventional polymers and there is no advantage. Above 90%wt, the viscosity decrease has reached a plateau and no longer drops with higher vinyl content. Therefore, there is no further advantage.

Anionic polymerization of conjugated diene hydrocarbons with lithium initiators is well known as described in U.S. Pat. Nos. 4,039,593 and Re. 27,145 which descriptions are incorporated herein by reference. Polymerization commences with a monolithium, dilithium, or polylithium initiator which builds a living polymer backbone at each lithium site. Typical living polymer structures containing polymerized conjugated diene hydrocarbons are:

X—B—Li

X—A—B—Li

X—A—B—A—Li

Li—B—Y—B—Li

Li—A—B—Y—B—A—Li wherein B represents polymerized units of one or more conjugated diene hydrocarbons such as butadiene or isoprene, A represents polymerized units of one or more vinyl aromatic compounds such as styrene, X is the residue of a monolithium initiator such as sec-butyllithium, and Y is the residue of a dilithium initiator such as the diadduct of sec-butyllithium and m-diisopropenylbenzene. Some structures, including those pertaining to polylithium initiators or random units of styrene and a conjugated diene, generally have limited practical utility although known in the art.

The anionic polymerization of the conjugated diene hydrocarbons is typically controlled with structure modifiers such as diethylether or ethyl glyme (1,2-diethoxyethane) to obtain the desired amount of 1,2-addition. (i.e. vinyl content). A 1,2-addition of about 40% may be achieved during polymerization at 50° C. with about 6% by volume of diethylether or about 200 ppm of ethyl glyme in the final solution. A 1,2 addition of about 47% may be achieved during polymerization by the presence of about 250 ppm of ortho-dimethoxybenzene (ODMB) in the final solution. A 1,2 addition of 78% may be achieved during polymerization by the presence of about 300 ppm of 1,2-diethoxypropane (DEP) in the final solution.

In general, the polymers useful in this invention may be prepared by contacting the monomer or monomers with an organoalkali metal compound in a suitable solvent, typically in the presence of a structure modifier, at a temperature in the range from −150° C. to 300° C., preferably at a temperature within the range from 0° C. to 100° C. Particularly effective polymerization initiators are organolithium compounds having the general formula:

RLi wherein R is an aliphatic, cycloaliphatic, alkyl-substituted cycloaliphatic, aromatic or alkyl-substituted aromatic hydrocarbon radical having from 1 to 20 carbon atoms.

Suitable solvents include those useful in the solution polymerization of the polymer and include aliphatic, cycloaliphatic, alkyl-substituted cyclo-aliphatic, aromatic and alkyl-substituted aromatic hydrocarbons, ethers and mixtures thereof. Suitable solvents, then, include aliphatic hydrocarbons such as butane, pentane, hexane, and heptane, cycloaliphatic hydrocarbons such as cyclohexane and cycloheptane, alkyl-substituted cycloaliphatic hydrocarbons such as methylcyclohexane and methylcycloheptane, aromatic hydrocarbons such as benzene and the alkyl-substituted aromatic hydrocarbons such as toluene and xylene, and ethers such as tetrahydrofuran, diethylether, and di-n-butyl ether.

When polar solvents like tetrahydrofuran are used, structure modifiers are typically not necessary for the preparation of high vinyl content butadiene and/or isoprene polymer blocks.

The hydrogenation of these polymers may be carried out by a variety of well established processes including hydrogenation in the presence of nickel catalysts such as Raney Nickel, noble metal catalysts such as those containing platinum, and/or palladium and soluble transition metal catalysts. Suitable hydrogenation processes which can be used are ones wherein the diene-containing polymer or copolymer is dissolved in an inert hydrocarbon diluent such as cyclohexane and hydrogenated by reaction with hydrogen in the present of a soluble hydrogenation catalyst. Such processes are disclosed in U.S. Pat. Nos. 3,113,986, 4,226,952 and Reissue 27,145, the disclosures of which are herein incorporated by reference. The polymers are preferably hydrogenated in such a manner as to produce hydrogenated polymers having a residual unsaturation content in polydiene blocks of less than about 1 percent, and most preferably as close to 0 percent as possible, of their original unsaturation content prior to hydrogenation. A titanium catalyst such as disclosed in U.S. Pat. No. 5,039,755, which is herein incorporated by reference, may also be used in the hydrogenation process.

The molecular weights of linear polymers or unassembled linear segments of polymers such as mono-, di-, triblock, etc., or the arms of star polymers before coupling are conveniently measured by Gel Permeation Chromatography (GPC), where the GPC system has been appropriately calibrated. For anionically polymerized linear polymers, the polymer is essentially monodisperse (weight average molecular weight/number average molecular weight ratio approaches unity), and it is both convenient and adequately descriptive to report the "peak" molecular weight of the narrow molecular weight distribution observed. Usually, the peak value is between the number and the weight average. The peak molecular weight is the molecular weight of the main species shown on the chromatograph. For polydisperse polymers the weight average molecular weight should be calculated from the chromatograph and used. The materials used in the columns of the GPC are styrene-divinyl benzene gels or silica gels. The solvent is tetrahydrofuran and the detector is a refractive index detector.

As discussed above, the adhesive of the present invention contains from greater than 6 to less than 15, preferably 8 to 11, percent by weight of a block copolymer of styrene and butadiene and/or isoprene having a vinyl content of greater than 50% by weight, preferably from 50 to 90%wt, more preferably 70 to 80 percent by weight. The adhesive comprises more than 6 weight percent block copolymer to get the desired pressure sensitive adhesive properties and for the adhesive to be sufficiently cohesive. The maximum amount of the polymer is less than 15 percent by weight in order to keep the viscosity of the adhesive sufficiently low for the positioning adhesive application. More polymer than 15 percent can be used and good adhesion properties will be obtained but the viscosity will be unnecessarily increased.

The base block copolymer must have a sufficient molecular weight and polystyrene content to be useful for pressure sensitive adhesives. Generally, the number average molecular weight should be in the range from 65,000 to 300,000 g/mol. If the molecular weight is less than 65,000 then the polymer loses its pressure sensitive adhesive properties. If the molecular weight is more than 300,000, then the polymer is not useful for adhesive applications.

The polystyrene content preferably ranges from 10 to 40 percent by weight because this confers the right balance of cohesion and processability to the polymer.

It is known that one method to characterize tackifying resin compatibility is by determination of cloud points in suitable solvent systems. From the cloud point values obtained, the resin may be characterized as being aliphatic, aromatic, or a combination of both, polar or nonpolar, and having a high or low molecular weight. Hydrocarbon resins display wide variation in cloud point values and thus the cloud point concept is a useful method to characterize hydrocarbon resins.

MMAP cloud point is a well known measure of aromatic solubility and determines the aliphatic/aromatic character of the resin. The lower the MMAP cloud point, which is expressed in degrees centigrade, the more aromatic is the resin. A 1:2 mixture of methylcyclohexane and aniline is used as the solvent system in the MMAP cloud point determination. A standard weight of resin is dissolved in the solvent at high temperature and allowed to cool with mixing. The temperature at which the resin begins to separate out as an extra phase is determined to be the MMAP cloud point. This may be seen in the mixture as a cloudiness in the previously clear solution.

Suitable tackifiers may be selected from the group consisting of compatible $C_5$ hydrocarbon resins, hydrogenated $C_5$ hydrocarbon resins, styrenated $C_5$ resins, $C_5/C_9$ resins, styrenated terpene resins, fully hydrogenated or partially hydrogenated $C_9$ hydrocarbon resins, rosins esters, rosins derivatives and mixtures thereof. The tackifying resin must have an MMAP cloud point that is at least 45° C. in order for the polymer/resin blend to be compatible. Commercially available hydrocarbon tackifying resins for the present invention include PICCOTAC® 95 (MMAP=95° C.) aliphatic resin, REGALREZ® series, like REGALREZ® 1085 (85° C.) or REGALREZ® 6108 (54° C.) and REGALITE® series, like REGALITE® V-1100 (48° C.) or REGALITE® S-260 (59° C.). REGALREZ® 3102 resin (MMAP=24° C.) does not work with this polymer because a phase stable blend cannot be achieved.

The suitable combination of resin type, block copolymer type and concentration in the formulation is required to obtain an easy, fast and homogeneous blend. For example, RP-6917, a high molecular SEBS weight polymer with 33 percent polystyrene content and a vinyl content of 70% by weight, can be easily mixed in a Z-blade mixer with PICCOTAC® 95, an aliphatic hydrocarbon resin and can quickly be homogeneously blended with REGALITE® V-1100. A hydrogenated pure aromatic resin containing a low level of aromaticity like REGALREZ® 1085 can also be used to get homogeneous blends.

Suitable plasticizers include plasticizing oils like low aromatic content (≦30%wt, preferably ≦10%wt) hydrocarbon oils that are paraffinic or naphthenic in character. Those products are commercially available from Shell Oil Company, like SHELLFLEX®, CATENEX® ONDINA® oils, KAYDOL® oil from Witco, or TUFFLO® oils from Arco. Other plasticizers include compatible liquid tackifying resins like REGALREZ® R-1018. Other ingredients might also be added, like olefin oligomers, low molecular weight polymers (≦30,000 g/mol) like liquid polybutene or liquid polyisoprene; copolymers, like liquid styrene/isoprene copolymers or hydrogenated styrene/isoprene copolymers, and liquid alpha-olefin polymers, vegetable oils and their derivatives, paraffin and microcrystalline waxes.

It is known in the art that various other components can be added to modify e.g the odor and/or the color of the adhesives. Antioxidants and other stabilizing ingredients can also be added to protect the adhesive from degradation induced by heat, light and processing or during storage. Several types of antioxidants can be used, either primary antioxidants like hindered phenols or secondary antioxidants like phosphite derivatives or blends thereof. Examples of commercially available antioxidants are IRGANOX® 565 from Ciba-Geigy (2.4-bis-(n-octylthio)-6-(4-hydroxy-3,5-di-tertiary-butyl anilino)-1,3,5-triazine), IRGANOX® 1010 from Ciba-Geigy (tetrakis-ethylene-(3,5-di-tertiary-butyl-4-hydroxy-hydrocinnamate)methane) and POLYGUARD® HR from Uniroyal (tris-(2,4-di-tertiary-butyl-phenyl) phosphite).

The adhesive composition of the present invention typically has a viscosity of 100 to 10,000 cPs at 177° C., preferably from 600 to 6,000 cPs at 177° C. The adhesive typically exhibits no transfer after being peeled away from a fabric. The adhesive composition is used in articles such as disposable diapers, sanitary napkins, bed pads, incontinent pads, surgical drapes, plasters, and bandages.

EXAMPLES

All molecular weights are number average. RP-6917 is a styrene-butadiene-styrene hydrogenated block copolymer having a molecular weight of 286,000, a polystyrene content of 33 percent by weight, a vinyl content of 70% by weight, and a polystyrene block molecular weight of 29,000. Several hydrocarbon tackifying resin types were evaluated with this polymer.

Example 1

All the ingredients were compounded in a Z-blade mixer. Then the samples were put in beaker in an oven at 180° C. Once molten, the adhesive was poured onto a Mylar sheet and cast to obtain a thickness of 2 mils (50 mi). Prior to testing, the samples were conditioned at 23° C. –50%RH (relative humidity) for 24 hours.

Standard peel, tack and cohesion tests were carried out on these formulations. To assess the right functionality of the adhesive, specific adhesion tests on fabrics were performed, namely to evaluate the adhesion of the positioning adhesive onto the undergarment. Cotton and nylon fabrics are the two reference materials used in these tests.

The following peel adhesion tests on fabric were carried out:

Peel adhesion initial: for cotton, the initial peel is preferred to be in the range of 200–500 g/lineal inch.

Peel adhesion retention or aging test: the samples (fabric/adhesive/Mylar) are put in an oven at 40° C./8 hours under a load of 160 g/sq. in. Peel adhesion is determined after 1 hour conditioning at 23° C. and 50RH. Occurrence of adhesive transfer to the fabric is reported as "none" or "transfer".

Adhesive transfer: the samples (fabric/adhesive/Mylar) are put in oven at 40° C./24 hours under a load of 800 g/sq. in. Peel adhesion is determined after 1 hour conditioning at 23° C. and 50%RH. Occurrence of adhesive transfer to the fabric is reported as "none" or "transfer".

The SAFT (shear adhesion failure temperature) was measured by 1"×1" Mylar to Mylar lap joint with a 1 kg weight. SAFT measures the temperature at which the lap shear assembly fails under load. Rolling Ball Tack (RBT) is the distance a steel ball rolls on the adhesive film with a standard initial velocity (Pressure Sensitive Tape Council Test No. 6). Small numbers indicate aggressive tack. Holding Power (HP) is the time required to pull a standard area (½ in.×½ in.) of tape from a standard test surface (steel, Kraft paper) under a standard load (1 kg), in shear at 2° (Pressure Sensitive Tape Council Method No. 7). Long times indicate high adhesive strength. 180° peel was determined by Pressure Sensitive Tape Council Method No. 1. Large numbers indicate high strength when peeling a test tape from a steel substrate. Polyken probe tack (PPT) was determined by ASTM D-2979. Loop tack (LT) was determined using PSTC-5 loop tack method. High numbers for PPT and LT indicate aggressive tack. T-peel is measured by ASTM D-1876.

Table 1 below shows the results for G-1650, an SEBS polymer with a lower vinyl content and molecular weight which is the current polymer of choice for commercial positioning adhesives, and RP-6917. PICCOTAC® 95 is a trademark for an aliphatic hydrocarbon tackifying resin which is manufactured by Hercules. V-1100 is a hydrogenated mixed cyclic aromatic tackifying resin which is manufactured by Hercules. REGALREZ® 6108 (R-6108) is a hydrogenated pure aromatic resin manufactured by Hercules. TUFFLO® 6056 oil is a plasticizing oil which is manufactured by ARCO.

Table 1 shows the results for RP-6917 based formulations in the range of 6 to 11.9% by weight polymer. Adhesive properties remain excellent for 10% by weight polymer (F-4, F-6) but adhesive transfer is observed at 6% by weight (F-5, F-7). The hot-melt viscosity decreases significantly with the reduction of RP-6917 level. F-4 and F-6 have good tack and adhesion on fabric, higher than the G-1650 reference Formulation F-1.

TABLE 2

Compatibility SBC/resin blends in function of the aromaticity of the resin as defined by the MMAP cloud point in ° C.

|  | R-3102 | V-1100 | R-6108 | S-260 | R-1085 | PICCOTAC 95 |
|---|---|---|---|---|---|---|
| MMAP | 24 | 48 | 54 | 59 | 85 | 95 |
| G-1650 | I | C | — | C | C | C |
| RP-6917 | I | C | C | C | C | C |
| Polymer A |  |  |  |  |  |  |

I = INCOMPATIBLE
C = COMPATIBLE

Example 3

Polymer B is an SEBS block copolymer equivalent in molecular parameters to the reference polymer KRATON G 1650 but with a higher vinyl content. The polymer contains 30% of polystyrene and a molecular weight of the polystyrene block of about 10,000, a total molecular weight of about 107,000, and the 1.2 butadiene of about 75%.

Polymer C is an SEBS block copolymers containing 20% of polystyrene, a molecular weight of the polystyrene block of about 10,000 and a total molecular weight of about 140,000, and a 1,2 butadiene content of 78%.

TABLE 1

|  | Formulation | | | | | | |
|---|---|---|---|---|---|---|---|
|  | F-1 | F-2 | F-3 | F-4 | F-5 | F-6 | F-7 |
| G-1650 | 100 | 100 |  |  |  |  |  |
| RP 6917Polymer A |  |  | 100 | 100 | 100 | 100 | 100 |
| PiccotacICCOTAC 95 | 349 | 559 |  |  |  |  |  |
| V1100 |  |  | 464 | 559 | 965 |  |  |
| R-6108 |  |  |  |  |  | 559 | 965 |
| TuffloUFFLO 6056 | 183 | 336 | 276 | 336 | 593 | 336 | 593 |
| IrganoxRGANOX 1010 | 3 | 3 | 3 | 3 | 3 | 3 | 3 |
| HMV 177° C. - cPs | 1,830 | 288 | 4,200 | 697 | 175 | 1,073 | 229 |
| 180 Peel (steel) - pli | 4.7 | 2.5 | 2.8 | 4 | 2.7 | 5.2 | 6.1 |
| 180 Peel Failure | Ghosting | Adh/Ghos | Cohesive | Cohesive | Cohesive | Cohesive | Cohesive |
| HP Steel, 1 kg (min) | 39 | 4 | 391 | 76 | 8 | 74 | 13 |
| HP Failure | A/G | Part adh | PC | G/A | Cohesive | G/A | Cohesive |
| SAFT Mylar 0.5 kg - ° C. | 67 |  | 65 | 60 | 54 | 64 | 46 |
| Loop Tack oz/in |  | 59 | 101 | 117 | 91 | 88 | 143 |
| Adhesion initial |  |  |  |  |  |  |  |
| T-Peel (cotton) pli | 0.5 | 0.7 | 1.2 | 1.7 | 2 T | 1.8 | 2.5 T |
| T-Peel (cotton) N/m | 88 | 123 | 210 | 298 | 350 | 315 | 438 |
| T-Peel (nylon) pli | 0.8 | 0.5 | 1.4 | 1 | 1.1 T | 1.8 | 2 T |
| T-Peel (nylon) N/m | 140 | 88 | 245 | 175 | 193 | 315 | 350 |
| Retention |  |  |  |  |  |  |  |
| T-Peel (cotton) pli | 0.34 | 0.5 |  | 1.3 |  | 1.3 |  |
| T-Peel (cotton) |  |  |  |  |  |  |  |
| T-Peel (nylon) pli | 0.7 | 0.6 |  | 1 |  | 1.4 |  |
| T-Peel (nylon) |  |  |  |  |  |  |  |
| Transfer |  |  |  |  |  |  |  |
| T-Peel (cotton) pli | 0.81 | 0.7 | 1.42 | 1.3 |  | 1.3 |  |
| T-Peel (cotton) |  |  |  |  |  |  |  |
| T-Peel (nylon) pli | 1.05 | 0.6 | 1.28 | 1.1 |  | 1.4 |  |
| T-Peel (cottonnylon) N/m | 184 | 105 | 224 | 193 |  | 245 |  |

T indicates transfer to the fabric

Example 2

In this example, blends of various tackifying resins with varying MMAP values were tested with several block copolymers for phase stability. The results are shown in Table 2 below.

Formulations F-8 and F-9 at 15.7% rubber content and Formulations F-10 and F-11 at 11.9% rubber content show very good adhesive properties without adhesive transfer on the fabric after peeling away. The viscosity is also very low particularly for Polymer B, the high vinyl version of KRA- TON G-1650. This indicates that high vinyl structure in the polymer decreases the hot-melt viscosity.

TABLE 3

|  | F-8 | F-9 | F-10 | F-11 |
|---|---|---|---|---|
| Polymer B | 100 |  | 100 |  |
| Polymer C |  | 100 |  | 100 |
| PICCOTAC 95 | 349 | 349 | 464 | 464 |
| TUFFLO 6056 | 183 | 183 | 276 | 276 |
| IRGANOX 1010 | 3 | 3 | 3 | 3 |
| Hot-melt viscosity 177° C.-cPs | 232 | 341 | 123 | 235 |
| Adhesion initial |  |  |  |  |
| T-Peel cotton pli | 0.6 | 0.5 | 0.7 | 0.6 |
| T-Peel cotton N/m | 105 | 88 | 123 | 105 |
| T-Peel nylon pli | 0.5 | 0.6 | 0.6 | 0.6 |
| T-Peel nylon N/m | 88 | 105 | 105 | 105 |
| Retention |  |  |  |  |
| T-Peel cotton pli | 0.8 | 1.1 | 0.8 | 0.7 |
| T-Peel cotton N/m | 142 | 228 | 142 | 123 |
| T-Peel nylon pli | 0.9 | 0.9 | 0.8 | 0.7 |
| T-Peel nylon N/m | 159 | 159 | 142 | 123 |
| Transfer |  |  |  |  |
| T-Peel cotton pli | 1.2 | 1.1 | 0.9 | 1 |
| T-Peel cotton N/m | 211 | 193 | 159 | 175 |
| T-Peel nylon pli | 1.3 | 0.9 | 1 | 0.8 |
| T-Peel nylon N/m | 228 | 159 | 175 | 142 |

Example 4

In this experiment, the viscosity temperature profiles of high vinyl block copolymers were compared to those of KRATON G-1650. It can been seen that first, the viscosity depends on the type of block copolymer tested. Indeed, Polymer B shows the lowest hot-melt viscosity, much lower than G-1650. It is followed by Polymer C. Secondly, the viscosity is also much lower at low temperature than KRATON G-1650. This is precisely the desired advantage so that adhesives containing them can be more easily processed at lower temperatures.

TABLE 4

|  | F-4 Polymer A | F-8 Polymer B | F-9 Polymer C | F-10 Polymer B | F-11 Polymer C | F-12 G-1650 | F-13 G-1650 |
|---|---|---|---|---|---|---|---|
| Rubber content % | 10 | 15.7 | 15.7 | 11.9 | 11.9 | 15.7 | 11.9 |
| Temperature °F. (° C.) |  |  |  |  |  |  |  |
| 275 (135) | 16,320 | 5,250 | 20,500 | 1,240 | 3,390 | 73,300 | 22,100 |
| 300 (149) | 3,385 | 1,250 | 4,670 | 410 | 930 | 16,240 | 4,800 |
| 325 (163) | 1,288 | 458 | 1,348 | 200 | 396 | 4,570 | 1,270 |
| 350 (177) | 697 | 232 | 641 | 123 | 235 | 1,800 | 575 |

We claim:

1. A hot melt pressure sensitive positioning adhesive for use with an absorbent article, comprising:

a) from greater than 6 to less than 15 percent by weight of the total of (a), (b) and (c) of a hydrogenated styrene-(butadiene and/or isoprene)- styrene block copolymer having a vinyl content of greater than 50% by weight;

b) from 50 to 80 percent by weight of the total of (a), (b) and (c) of a tackifying resin which has an aromaticity such that the MMAP cloud point is at least 45 degrees Celsius; and c) from 5 to 35 percent by weight of the total (a), (b) and (c) of a plasticizer.

2. The adhesive of claim 1 wherein the vinyl content of the block copolymer is from 70 to 80 percent by weight.

3. The hot melt adhesive of claim 1 wherein the viscosity of the adhesive is from 100 to 10,000 cPs at 177° C.

4. The adhesive of claim 3 wherein the viscosity of the adhesive is from 600 to 6000 cPs at 177° C.

5. The adhesive of claim 1, wherein the block copolymer has a number average molecular weight between 65,000 g/mol to 300,000 g/mol.

6. The adhesive of claim 1, wherein the adhesive has a polystyrene content between 10 percent and 40 percent by weight of the copolymer.

7. A hot melt pressure sensitive positioning adhesive, comprising:

a) from 8 to 11 percent by weight of a hydrogenated styrene-(butadiene and/or isoprene)-styrene block copolymer having a vinyl content of greater than 50% by weight;

b) from 50 to 80 percent by weight of a tackifying resin having an aromaticity such that the MMAP cloud point is at least 45° C.; and c) from 5–35 percent by weight of a plasticizer.

8. The adhesive of claim 7, wherein the vinyl content of the block copolymer is from 70 to 80 percent by weight.

9. The adhesive of claim 7, wherein the viscosity of the adhesive is from 100 to 10,000 cPs at 177° C.

10. The adhesive of claim 7, wherein the viscosity of the adhesive is from 600 to 6,000 cPs at 177 ° C.

11. The adhesive of claim 7, wherein the block copolymer has a number average molecular weight between 65,000 g/mol to 300,000 g/mol.

12. The adhesive of claim 7, wherein the block copolymer has a number average molecular weight greater than 65,000 g/mol.

13. The adhesive of claim 7, wherein the adhesive has a polystyrene content between 10 percent and 40 percent by weight of the copolymer.

* * * * *